US012687539B2

(12) United States Patent
Zhang et al.

(10) Patent No.: US 12,687,539 B2
(45) Date of Patent: Jul. 21, 2026

(54) IMMUNOADSORBENT AND COMPOSITE AFFINITY COLUMN FOR PURIFYING FUMONISINS B1, ANGUIDIN, T-2 TOXIN, ZEARALENONE AND VOMITOXIN, METHOD FOR DETECTING THE SAME, AND PREPARATION METHOD OF COMPOSITE AFFINITY COLUMN

(71) Applicant: OIL CROPS RESEARCH INSTITUTE, CHINESE ACADEMY OF AGRICULTURAL SCIENCES, Hubei (CN)

(72) Inventors: Qi Zhang, Hubei (CN); Yizhen Bai, Hubei (CN); Nanri Yin, Hubei (CN); Fei Ma, Hubei (CN); Peiwu Li, Hubei (CN)

(73) Assignee: OIL CROPS RESEARCH INSTITUTE, CHINESE ACADEMY OF AGRICULTURAL SCIENCES, Hubei (CN)

( * ) Notice: Subject to any disclaimer, the term of this patent is extended or adjusted under 35 U.S.C. 154(b) by 1011 days.

(21) Appl. No.: 17/777,056

(22) PCT Filed: Nov. 16, 2020

(86) PCT No.: PCT/CN2020/129075

§ 371 (c)(1),
(2) Date: Sep. 29, 2022

(87) PCT Pub. No.: WO2021/093887

PCT Pub. Date: May 20, 2021

(65) Prior Publication Data

US 2023/0273189 A1 Aug. 31, 2023

(30) Foreign Application Priority Data

Nov. 15, 2019 (CN) ......................... 201911121740.X

(51) Int. Cl.
*G01N 33/53* (2006.01)
*G01N 33/543* (2006.01)
*G01N 33/68* (2006.01)

(52) U.S. Cl.
CPC ..... *G01N 33/5308* (2013.01); *G01N 33/5436* (2013.01); *G01N 33/6848* (2013.01); *G01N 2333/37* (2013.01)

(58) Field of Classification Search
CPC ................................................. G01N 2333/37
See application file for complete search history.

(56) References Cited

U.S. PATENT DOCUMENTS

| | | | | |
|---|---|---|---|---|
| 6,596,476 | B1 * | 7/2003 | Lesniewski ........ | G01N 33/5767 435/5 |
| 2018/0092950 | A1 | 4/2018 | Davis et al. | |

FOREIGN PATENT DOCUMENTS

| | | |
|---|---|---|
| CN | 106970223 | 7/2017 |
| CN | 106977600 | 7/2017 |
| CN | 110133249 | 8/2019 |
| EP | 2942627 | 11/2015 |
| WO | 2015075686 | 5/2015 |

OTHER PUBLICATIONS

Harlow et al. (Harlow, E. and Lane, D., Antibodies: A Laboratory Manual (1988) Cold Spring Harbor Laboratory Press, Cold Spring Harbor, NY, pp. 23-26.) (Year: 1988).*
Lederman et al. ("A single amino acid substitution in a common African allele of the CD4 molecule ablates binding of the monoclonal antibody, OKT4" Mol Immunol. Nov. 1991;28(11):1171-81) (Year: 1991).*
Colman et al. (Research in Immunology, 1994; 145(1): 33-36) teach that amino acid changes in an antigen can effectively abolish antibody antigen binding entirely (see entire document, particularly pp. 33-34) (Year: 1994).*
Brown et al. (J Immunol. May 1996;156(9):3285-91 at 3290 and Tables 1 and 2) (Year: 1996).*
Dixon-Holland et al (Production of Sensitive Monoclonal Antibodies to Aflatoxin B1and Aflatoxin M1 and Their Application to ELISA of Naturally Contaminated Foods. Journal of Food Protection. vol. 51, Issue 3, Mar. 1, 1988, pp. 201-204 (Year: 1988).*
"International Search Report (Form PCT/ISA/210) of PCT/CN2020/129075", mailed on Feb. 19, 2021, with English translation thereof, pp. 1-7.

* cited by examiner

*Primary Examiner* — Bao-Thuy L Nguyen
(74) *Attorney, Agent, or Firm* — JCIP GLOBAL INC.

(57) ABSTRACT

An immunoadsorbent and a composite affinity column for purifying fumonisin B1, anguidin, T-2 toxin, zearalenone, and vomitoxin. The immunoadsorbent includes a solid phase carrier, and a fumonisin B1 monoclonal antibody, an anguidin monoclonal antibody, a T-2 toxin monoclonal antibody, a zearalenone monoclonal antibody and a vomitoxin monoclonal antibody which are coupled to the solid phase carrier, the anguidin monoclonal antibody is a monoclonal antibody secreted by a hybridoma cell strain DAS5G11E7 having an accession number of CCTCCNO:C201881. The affinity column can be used for high performance liquid chromatography-mass spectrometry detection of the fumonisin B1, the anguidin, the T-2 toxin, the zearalenone and the vomitoxin, and has stable performance. Furthermore, an economical, quick, precise and safe detection method is established of the basis of the affinity column, and can be used for purifying and detecting samples of the five toxins without mutual interference and influence.

10 Claims, 2 Drawing Sheets

Specification includes a Sequence Listing.

IMMUNOADSORBENT AND COMPOSITE AFFINITY COLUMN FOR PURIFYING FUMONISINS B1, ANGUIDIN, T-2 TOXIN, ZEARALENONE AND VOMITOXIN, METHOD FOR DETECTING THE SAME, AND PREPARATION METHOD OF COMPOSITE AFFINITY COLUMN

CROSS-REFERENCE TO RELATED APPLICATION

This application is a 371 of international application of PCT application serial no. PCT/CN2020/129075, filed on Nov. 16, 2020, which claims the priority benefit of China application no. 201911121740.X, filed on Nov. 15, 2019. The entirety of each of the above mentioned patent applications is hereby incorporated by reference herein and made a part of this specification.

FIELD

The present disclosure relates to an immunoadsorbent and a composite affinity column for purifying fumonisin B1, anguidin, T-2 toxin, zearalenone and vomitoxin.

BACKGROUND

Fumonisin B1 is a water-soluble metabolite produced by *Fusarium* B1 under a certain temperature and humidity, it is a sort of diester compounds which are composed of different polyols and tricarboxylic acids and have similar structures. The fumonisin B1 can disturb normal physiological functions of plants in a low concentration range, it is a nonenzymatic compound without toxic action to plant metabolism, and belongs to mycotoxins and non-host-specific toxins. It chiefly distributes in crops mainly based on maize, sorghum and wheat, and can cause agricultural economical loss such as seedling blight, decay of root, stem, seed, etc. The fumonisin B1 may cause various specific toxicological effects to livestock and poultry and laboratory animals, such as leukoencephalomalacia of horse and rabbit, its performance is: symptoms such as neurotoxicity, disturbance of consciousness, blindness and ataxia, and in severe cases, it even causes death. It may also cause edema and hydrothorax of pig, injury of liver and oesophagus. The fumonisin B1 may also cause atherosclerosis of primates, hepatocyte apoptosis and renal toxicity of rat, lamb and calf, it also has hepatotoxicity and a carcinogenic effect, bringing about severe economic loss to animal husbandry.

Anguidin (DAS), also known as diacetoxyscirpenol, is a metabolite from some bacterial species like *Fusarium*, and belongs to trichothecenes compounds. The anguidin is an important trichothecenes compound, which has a high contamination level and a great damage in the *Fusarium* toxin, and its acute toxicity is strong. Anguidin is a colorless crystalline, poorly soluble in water, soluble in polar solvent (such as methanol, etc.), the material is very stable, in a cooking process, it may not be destroyed, LDS of anguidin to rat is 0.75 mg/kg, and the heat stability is also strong. A small amount of investigation on contaminated level of anguidin in grain and feed is carried out only in USA, Germany, Italy and India, its content is 0.05-31.5 mg/kg. Toxicity of anguidin is strong, it belongs to fat soluble toxins, the toxic symptoms resulting from anguidin is similar to T-2 toxin, but more severe, the clinical manifestations after intoxication are serious dermatitis, nausea, vomiting, bloody diarrhea, bone marrow hematopoietic system damage, nervous system disorder, anorexia and death.

T-2 toxin is one of trichothecenes with a strongest toxicity produced by *Fusarium*, it is found and reported by Bamburg et al in 1968. Fungi which produce T-2 toxin chiefly live on the grains in the field, most of them belong to *Fusarium*, such as *Fusarium sporotrichioides, Fusarium poae* and *Fusarium trifolium*. The optimum toxigenic environment of *Cladosporium* is humidity of 40%-50% and temperature of 3-7° C.; the toxigenic ability in maize and dye is strongest, followed by barley, rice and wheat. It may cause intoxication of animals such as chicken, pig, rabbit, cat, rat, mouse, monkey, etc. Its toxicity is mainly manifested in: cytotoxicity, dermal toxicity, phytotoxicity, immune suppression and emesis. So far it is found that T-2 toxin may be associated with four known human diseases: one is alimentary toxic aleukia (ATA); another is osteopathy such as Kashin-Beck disease (KBD), and cartilage injury; the third is an impaired reproductive development system; the fourth is DNA damage of peripheral blood lymphocyte.

Zearalenone, also known as F-2 toxin, is firstly separated from maize with *Fusarium* head blight. Toxigenic bacteria of zearalenone are mainly bacterial strains of *Fusarium*, such as *Fusarium graminearum* and *Fusarium trifolium*. Zearalenone mainly contaminates grain such as maize, wheat, rice, barley, millet and oats, where a positive detection rate of the maize is 45%, the highest poison content may reach 2909 mg/kg; the detection rate of the wheat is 20%, the poison content is 0.364-11.05 mg/kg. Heat resistance of zearalenone is strong, it is completely destroyed only after being treated at 110° C. for 1 h. Zearalenone has an estrogen-like effect, which mainly acts on a reproductive system, and enables livestock, poultry and laboratory mice to produce hyperestrogenism. Eating a food containing zearalenone by animals (including human) at gestation period may cause miscarriage, dead embryo and foetal deformities. Eating various cooked wheaten food made of wheat flour containing *fusarium* head blight may also cause toxic symptoms of central nervous system, such as nausea, cold feeling, headache, depression and ataxia.

Deoxynivalenol is a metabolite produced by *Fusarium nivale* and *Fusarium avenaceum* which often contaminate wheat when they live on grains. Deoxynivalenol, also known as vomitoxin (DON), is a secondary metabolite of *Fusarium*. DON is mostly produced slowly by cereal crops at a low-temperature, damp and harvest time, it mainly contaminates crops such as maize and wheat, it generally has a high concentration in wheat, barley, oats and maize, and has a low concentration in rye, sorghum and rice, it also contaminates food products, such as bread, biscuit, wheaten dessert, etc., in addition, DON residue is found in both milk and egg of animals. Toxicity of the DON is low, but it is most likely to appear, hence its incidence in agricultural products is highest. The toxic effect of DON mainly impacts the immune system and gastrointestinal tract of animals.

At present, these mycotoxin detection methods are mainly thin-layer chromatography, enzyme linked immunosorbent assay (ELISA), immunoaffinity chromatography-liquid chromatography, immunoaffinity chromatography-fluorescence spectrophotometry, etc. The thin-layer chromatography needs to contact a lot of standard substances, which is harmful to health of an experimenter, and its sensitivity is very low. The enzyme linked immunosorbent assay is only applicable to qualitative detection, and false positive and false negative results are very prone to occurring.

Immunoaffinity chromatography liquid-chromatography is to combine a immune reaction with a chromatography, using the high specificity and affinity of antigen-antibody binding, binding a specific antibody to a chromatographic adsorbent by a chemical coupling bonding method, thereby realizing an effective separation and enrichment and purification of a target material in a complex sample based on immunologically reversible binding. Thus, it is possible to specifically separating a mycotoxin from the sample, so as to avoid use of toxic solvents such as chloroform and dichloromethane. Therefore, preparation of a purifying immunoaffinity column with a stable performance is a premise for establishing an economical, quick, precise and safe liquid chromatography detection method for muti-toxin mixed contamination of fumonisin B1, anguidin, T-2 toxin, zearalenone and vomitoxin.

SUMMARY

Aiming at the shortcoming in the related art, the present disclosure provides an immunoadsorbent and a composite affinity column for purifying fumonisin B1, anguidin, T-2 toxin, zearalenone and vomitoxin, as well as preparation method and application thereof.

In order to realize the above objective, the technical solution adopted by the present disclosure includes:

an immunoadsorbent for purifying fumonisin B1, anguidin, T-2 toxin, zearalenone and vomitoxin is provided, the immune adsorbent includes a solid phase carrier, and an anti-fumonisin B1 monoclonal antibody, an anti-anguidin monoclonal antibody, an anti-T-2 toxin monoclonal antibody, an anti-zearalenone monoclonal antibody, and an anti-vomitoxin monoclonal antibody which are coupled to the solid phase carrier, and the anti-anguidin monoclonal antibody (anti-diacetoxyscirpenol monoclonal antibody) is a monoclonal antibody secreted by a hybridoma cell strain DAS5G11E7 having an accession number of CCTCCNO:C201881. The hybridoma cell strain DAS5G11E7 has been preserved at China Center for Type Culture Collection (CCTCC) in Apr. 3, 2018, the preservation address is Wuhan University, Wuhan, China, and the accession number is CCTCC NO.C201881.

According to the above solution, the solid phase carrier is sepharose.

A composite affinity column for purifying fumonisin B1, anguidin, T-2 toxin, zearalenone, and vomitoxin is provided, the composite affinity column is loaded with an immunoadsorbent for purifying fumonisin B1, anguidin, T-2 toxin, zearalenone, and vomitoxin.

Preparation of the composite affinity column for purifying fumonisin B1, anguidin, T-2 toxin, zearalenone, and vomitoxin, includes:

a) Matrix treatment washing CNBr-activated sepharose matrix powder with HCl under at a pH of 2-3 to remove impurities, the CNBr-activated sepharose matrix powder is provided in a lyophilized form;

b) Ligand coupling dissolving a fumonisin B1 monoclonal antibody, an anguidin monoclonal antibody, a T-2 toxin monoclonal antibody, a zearalenone monoclonal antibody, and a vomitoxin monoclonal antibody to be coupled using a coupling buffer to obtain antibody solutions, quickly transferring the sepharose matrix activated in the step a) to the above antibody solutions, and carrying out coupling;

c) Ligand blocking blocking all remaining active groups;

d) removing excess ligands that are not coupled after the coupling; and e) packing.

According to the above solution, the washing is carried out with HCl having a concentration of 1 mmol/L for 15 min in the step a).

According to the above solution, the coupling buffer in the step b) is 0.2 mol/L $Na_2HCO_3$ with a pH of 8.3.

According to the above solution, the concentration of each antibody solution in the step b) is 10-15 mg/mL.

According to the above solution, a coupling condition in the step b) includes: fully mixing the above mixture under a room temperature condition of (20-25° C.) for 2-4 h.

According to the above solution, a ligand blocking process in the step c) includes: transferring the sepharose matrix treated by the step b) to a 0.1 mol/L Tris-HCl buffer, standing for 2-4 h under a room temperature condition.

According to the above scheme, the step d) includes: successively washing the sepharose matrix after being treated by the step c) with a buffer solution with a pH value of 4 and a buffer solution with a pH value of 8 for at least three cycles;

The buffer solution with a pH value of 4 and the buffer solution with a pH value of 8 may be respectively selected from 0.1 mol/L acetic acid/sodium acetate buffer and 0.1 mol/L Tris-HCl buffer.

According to the above solution, after treatment in the step e), washing is carried out with a 0.01% $NaN_3$—PBS of which the amount is 5 times the volume of the sepharose, preserving is carried out by using 0.01% $NaN_3$—PBS, and then packing is carried out.

According to the above solution, preferably, $IC_{50}$ of the anti-deoxynivalenol (vomitoxin) monoclonal antibody is less than or equal to 15 ppb; $IC_{50}$ of the anti-T-2 toxin monoclonal antibody is less than or equal to 2 ppb; the anti-fumonisin B1 monoclonal antibody may be selected from a monoclonal antibody secreted by a hybridoma cell strain Fm7A11 having an accession number of CCTCC NO.C201636; and the anti-zearalenone monoclonal antibody is selected from a monoclonal antibody secreted by a hybridoma cell strain 2D3 having an accession number of CCTCC NO.C201328.

On the basis of this, the present disclosure establishes a method for detecting the content of fumonisin B1, anguidin, T-2 toxin, zearalenone and vomitoxin by an immunoaffinity column purifying-LM method, when the sample to be detected passes through the immunoaffinity column, the immunoadsorbent may specifically absorb fumonisin B1, anguidin, T-2 toxin, zearalenone, and vomitoxin, other impurities flow out of the immunoaffinity column, then the immunoaffinity column is eluted with a chromatographic grade methanol, the eluting flow rate is 1 mL/min-2 mL/min, and fumonisin B1, anguidin, T-2 toxin, zearalenone, and vomitoxin are eluted from the column, so as to fully purifying the sample, and thus the collected eluent is used for detection by a high-performance liquid chromatograph-mass spectrometer.

Based on the above method for detecting the content of fumonisin B1, anguidin, T-2toxin, zearalenone, and vomitoxin with a composite affinity column, when a sample to be detected passes through the immunoaffinity column, the immunoadsorbent may specifically absorb fumonisin B1, anguidin, T-2 toxin, zearalenone, and vomitoxin, other impurities flow out of the immunoaffinity column, then the composite affinity column with a chromatographic grade methanol, the eluent is collected, i.e. a sample after the purifying and concentrating is used for detection by a high-performance liquid chromatograph-mass spectrometer to obtain the content of each toxin;

conditions for the high-performance liquid chromatograph-mass spectrometer:

a) mobile phase: A, 0.05% of a formic acid/water solution; B, 0.05% of a formic acid/acetonitrile solution;
b) gradient elution: 0-3 min, 15%-50% of B; 4-5 min, 50%-70% of B; 6.5-8 min, 70%-100% of B; 8-10 min, 100%-50% of B; 10-11 min, 50%-15% of B; 11-15 min, 15% of B;
c) chromatographic column: C-18 column;
d) flow rate: 150-200 μL/min;
e) mass spectrometry scanning parameters of the detection for various toxins are as shown in Table 1.

TABLE 1

Scanning parameters of various toxins

| Toxin | Parent ions (m/z) | Quantitative daughter ions (m/z) | Cone voltage (V) | Collision energy (V) |
|---|---|---|---|---|
| DON | 297.28 | 249.1 | 20 | 10 |
| | | 203.1 | 20 | 14 |
| DAS | 367.2 | 307.2 | 30 | 10 |
| | | 289.1 | 30 | 10 |
| T-2 | 489.31 | 387.2 | 42 | 22 |
| | | 245.1 | 42 | 34 |
| ZEN | 317.0 | 130.8 | 30 | 30 |
| | | 174.9 | 30 | 25 |
| | | 310.1 | 30 | 24 |
| FB1 | 722.05 | 334.0 | 30 | 35 |
| | | 352.0 | 30 | 35 |
| | | 265.0 | 30 | 25 |

A specific quantitative method may adopt the following modes: absorbing different concentrations of fumonisin B1, anguidin, T-2 toxin, zearalenone and vomitoxin standard working liquids with a sample injector, injecting them into a high-performance liquid chromatograph-mass spectrometer, measuring a peak area of a standard solution under the above conditions, drawing standard curves of the various toxins, and then calculating the content of each toxin using an external standard method.

According to the above solution, the eluting flow rate is 1 mL/min-2 mL/min.

Beneficial effects of the present disclosure: the affinity column prepared by the present disclosure can be used for the high performance liquid chromatography-mass spectrometry detection of fumonisin B1, anguidin, T-2 toxin, zearalenone, and vomitoxin, and has stable performance. Furthermore, the present disclosure establishes an economical, quick, precise and safe detection method on the basis of the affinity column, and can be used for purifying and detecting samples of the five toxins without mutual interference and influence.

Figure 2:
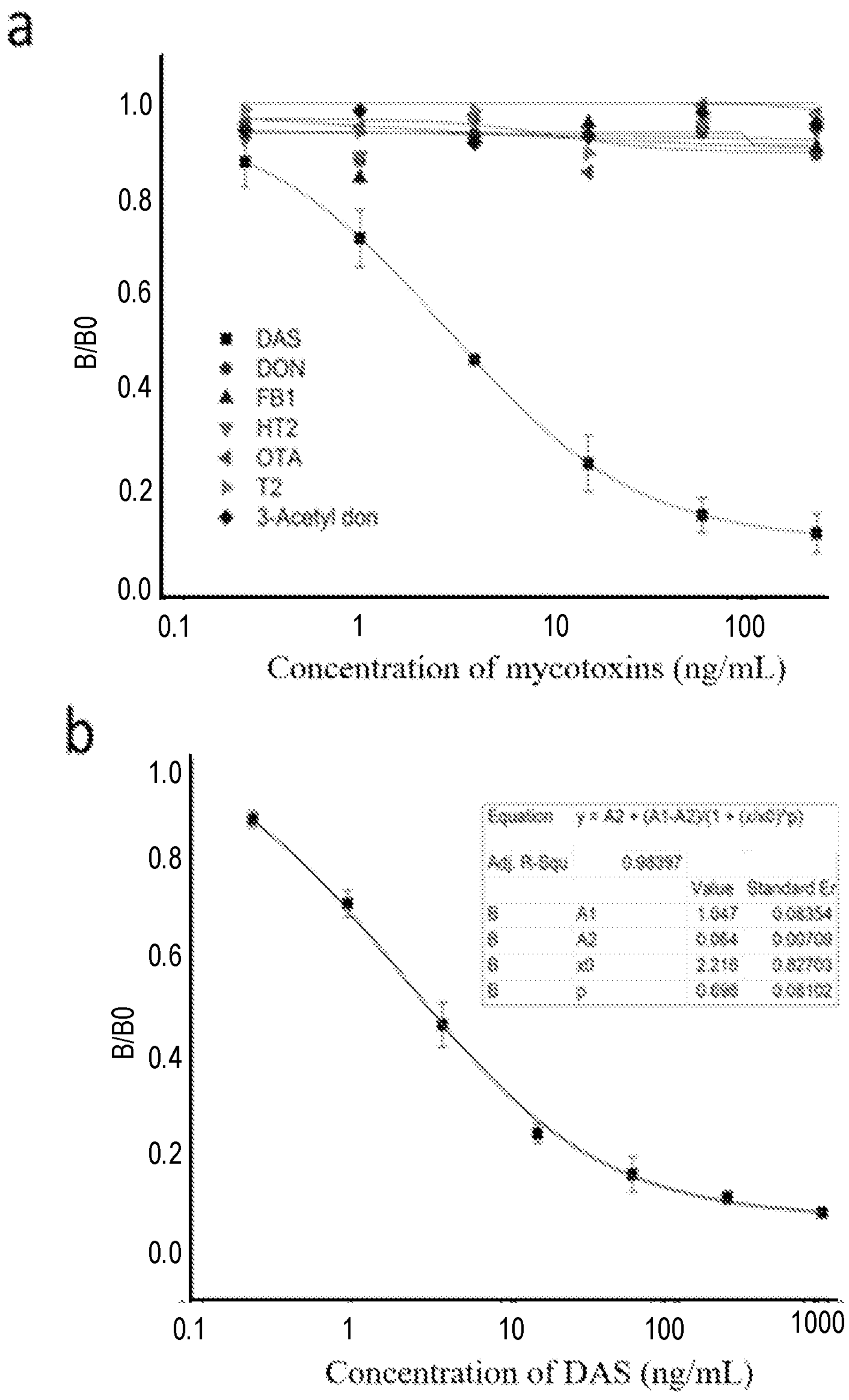

(a) of FIG. 2 is a result of a cross reaction between a diacetoxyscirpenol monoclonal antibody and other mycotoxins provided by the present disclosure; and (b) of FIG. 2 is a standard curve of diacetoxyscirpenol enzyme-linked immunosorbent assay established by the diacetoxyscirpenol monoclonal antibody provided by the present disclosure.

DETAILED DESCRIPTION OF THE EMBODIMENTS

Obtaining of an Anti-Diacetoxyscirpenol Monoclonal Antibody

The anti-diacetoxyscirpenol monoclonal antibody is secreted by a hybridoma cell strain DAS5G11E7 with an accession number of CCTCC NO.C201881, and the preparation method includes:

the hybridoma cell strain DAS5G11E7 is injected into a BALB/c mouse which is pretreated with a Freund's incomplete adjuvant, an ascites of the mouse is collected, the antibody is purified using a caprylic acid-ammonium sulfate method, the specific operation includes: the mouse ascites is filtered with double-layer filter paper, centrifuged at 4° C. under 12000 r/min for more than 15 min, a supernatant is absorbed, the obtained ascites supernatant is mixed with an acetate buffer having 4 times volume of the ascites supernatant, and n-caprylic acid is added slowly under stirring, the volume of n-caprylic acid per milliliter ascites is 30-35 μL, mixed at room temperature for 30-60 min, standing is carried out at 4° C. for more than 2 h, under 12000 r/min, centrifuging is carried out at 4° C. for more than 30 min, a precipitate is abandoned, the obtained supernatant is filtered with double-layer filter paper, a phosphate buffer having a volume of 1/10 of the filtrate and molar concentration of 0.1 mol/L and pH of is7.4 is added, the pH of the mixed liquid is adjusted to be 7.4 with a 2 mol/L sodium hydroxide solution, ammonium sulfate is added slowly to an ice bath until a final concentration of ammonium sulfate is 0.277 g/mL, standing is carried out at 4° C. for more than 2 h, then centrifuged under 12000 r/min at 4° C. for more than 30 min, the supernatant is abandoned, the obtained precipitate is re-suspended in a phosphate buffer having a 1/10 volume of the original ascites, molar concentration of 0.01 mol/L and pH of 7.4, and put in a dialysis bag, dialyzed with a 0.01 mol/L PBS for two days, and then dialyzed with PB for two days, a protein solution in the dialysis bag is taken out, and centrifuged, a supernatant is collected, a precipitate is abandoned, and the mixture is pre-frozen at −70° C. then put in a lyophilizer for freeze drying. Lyophilized powder, i.e. a purified anti-diacetoxyscirpenol monoclonal antibody is collected.

The acetate buffer is obtained by adding water into 0.29 g of sodium acetate and 0.141 mL of acetic acid to a volume of 100 mL; and the 0.01 mol/L of phosphate buffer is obtained by adding water into 0.8 g of sodium chloride, 0.29 g of disodium hydrogen phosphate dodecahydrate, 0.02 g of potassium chloride and 0.02 g of potassium dihydrogen phosphate to a volume of 100 mL.

Based on the identification by a commercially available subtype identification kit, the subtype of the anti-diacetoxyscirpenol monoclonal antibody secreted by the hybridoma cell strain DAS5G11E7 is IgG2b.

The antibody titer after purification of mouse ascites detected by the routine uncompetitive enzyme-linked immunosorbent assay (ELISA) may reach $3.2\times10^5$, i.e., when the antibody is diluted for $3.2\times10^5$ times, the solution detection results are positive. By routine indirect competitive ELISA, its sensitivity to diacetoxyscirpenol is 3.08 ng/mL. The cross reactions with other mycotoxins, T2 toxin, HT2 toxin, vomitoxin, 3-acetyldeoxynivalenol, ochratoxin and fumonisin are all less than 0.01% (Table 2; FIG. 2). The specificity of the antibodies can be evaluated by a cross reactivity. The DAS5G11E7 monoclonal antibody is detected using the indirect competitive ELISA method, standard solutions of series concentrations are prepared by DAS, T2 toxin, HT2 toxin, DON, 3-ACDON, OTA andFB1, respectively added into an ELISA plate together with equal volume of the antibodies, and incubated for 1 h, and the other steps are identical to the indirect competitive ELISA method. Using the above toxin standard solution concentration as an abscissa, using an OD value B/B0 detected at 450 nm by a microplate reader as an ordinate, a competitive inhibition curve is drawn, and the cross reactivity is determined by calculating ratio of $IC_{50}$ value of DAS to other toxins. The calculation formula is as follows:

$$CR\ \% = (IC_{50}DAS/IC_{50}\ \text{other toxin}) \times 100.$$

TABLE 2

Cross reaction of DAS5G11E7 with other toxins.

| Name of toxin | Structure | $IC_{50}$ | Cross reactivity |
|---|---|---|---|
| DAS | 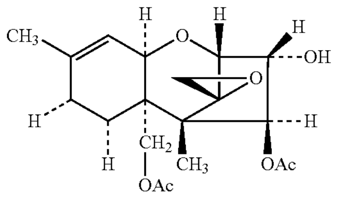 | 3.08 | 100% |
| T-2 toxin | 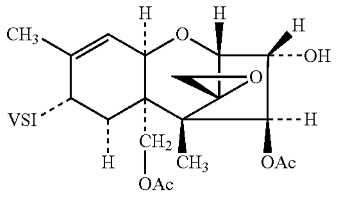 | >100.00 | <0.01% |
| HT-2 toxin | 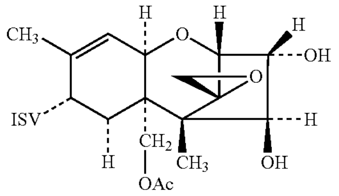 | >100.00 | <0.01% |
| DON | 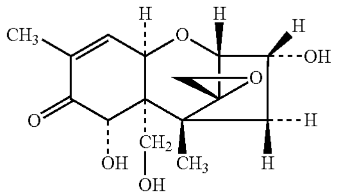 | >100.00 | <0.01% |
| 3-acetyl-DON | 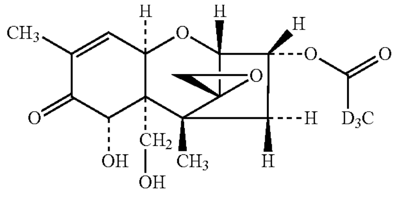 | >100.00 | <0.01% |

TABLE 2-continued

Cross reaction of DAS5G11E7 with other toxins.

| Name of toxin | Structure | $IC_{50}$ | Cross reactivity |
|---|---|---|---|
| FB1 | 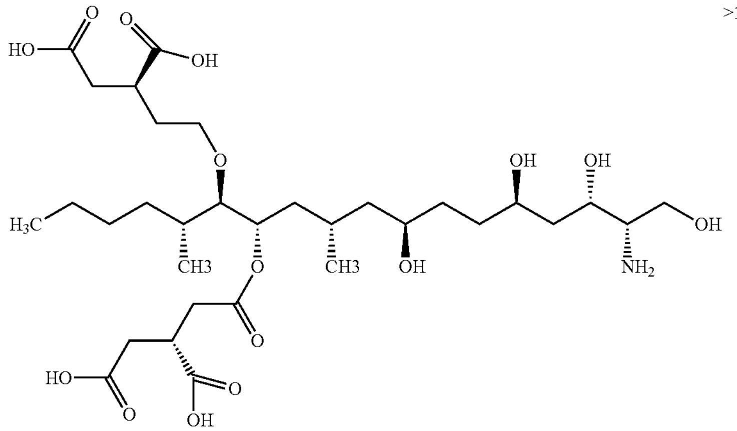 | >100.00 | <0.01% |
| OTA | 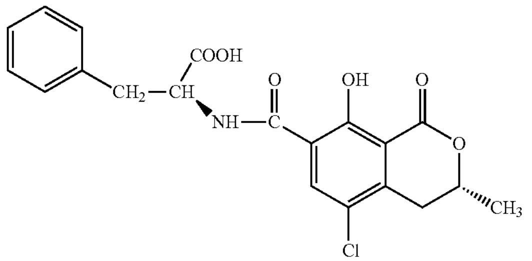 [SMILES: C[C@@H]1Cc2c(Cl)cc(C(=O)N[C@@H](Cc3ccccc3)C(=O)O)c(O)c2C(=O)O1] | >100.00 | <0.01% |

Figure 1:
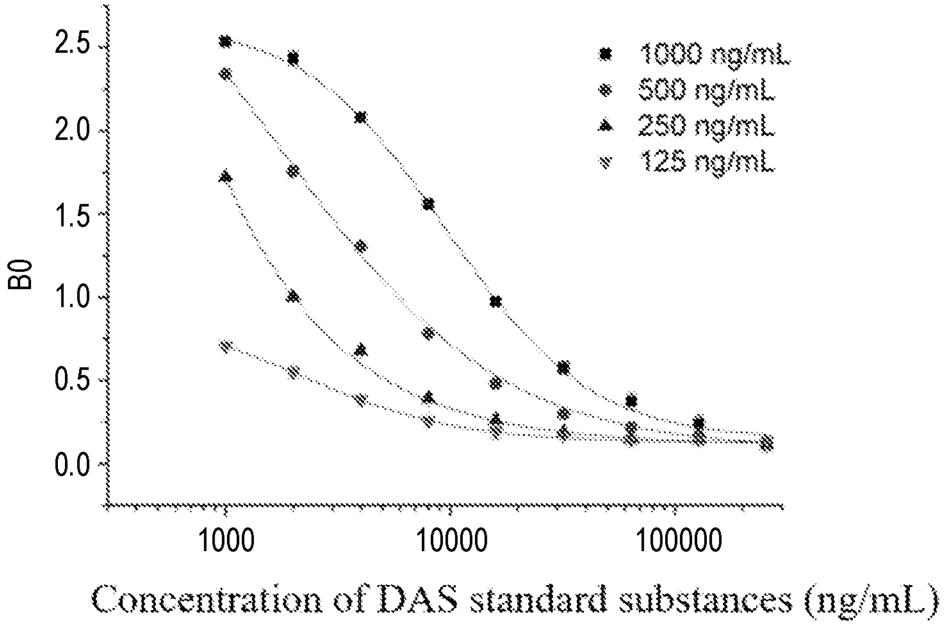
FIG. 1 is affinity measurement data of a diacetoxyscirpenol monoclonal antibody provided by the present disclosure.

Affinity of DAS5G11E7 is measured by an indirect noncompetitive ELISA method. The ELISA plate is coated with DAS-OVA according to concentrations of 1.0, 0.5, 0.25, 0.125 μg/mL, at 100 μL/well and 37° C. for 2 h; the ELISA plate is blocked with a liquid block for 1 h, then the antibodies diluted with PBS (dilution factor 1:2) is added into the ELISA plate, the remaining steps are identical to the indirect noncompetitive ELISA method. The measured OD450 value is used as the ordinate, A logarithmic value of the antibody concentration (mol/L) is used as the abscissa, and S-shaped curves of four concentrations are made. maximum OD values at the top of each S-curve (i.e., $OD_{max}$) are found out, and the antibody concentrations corresponding to 50% $OD_{max}$ value in each curve are found out. Any two concentrations in the four concentrations are put into one group, affinity constants of the antibodies are calculated according to a formula Ka=(n−1)/2(n[Ab']t−[Ab]t), where [Ab']t and [Ab]t are the antibody concentrations corresponding to 50% maximum OD value in each group, n is the times of coated antigen concentration in each group (including three ratios of 1:2, 1:4 and 1:8), six Ka values are obtained totally. The obtained six Ka values are averaged, the affinity of the diacetoxyscirpenol mouse ascites antibody obtained by enzyme linked immunosorbent assay (ELISA) method may reach $5.4\times10^8$ L/moL (FIG. 1).

Screening of a Hybridoma Cell Strain DAS5G11E7

1. Animal Immunization 6-7-week-old BALB/c mice are immunized using a diacetoxyscirpenol complete antigen DAS-BSA prepared in the laboratory. In a first immunization, the diacetoxyscirpenol complete antigen is emulsified with an equal volume of Freund's complete adjuvant, and injected at multiple sites on the nape of the neck of the mouse subcutaneously. 4 week later, a second immunization is carried out, the Freund's incomplete adjuvant is used to be emulsified with an equal volume of diacetoxyscirpenol complete antigen, and injected at mouse abdomen. There is a four-week interval between a third immunization and the second immunization, the immunization method is the same with it, a fourth immunization is carried out 3 weeks after the third immunization, the immunization method is the same with the second immunization, and similarly injected at the abdomen. The doses for the four immunizations are the same, which are 70 μg per mouse. For the first 3 times each time 8-10 days after the immunization, blood is collected from the tail vein, a serum is separated, the serum titer of the mouse is detected using the indirect ELISA method. 8 days after the third immunization, the tail is cut, and blood is collected, a mouse corresponding to the serum having a relatively high titer and sensitivity is selected to carry out a final booster immunization, and the immunizing dose is 2 times preceding one.

2. Cell Fusion

Three days after the booster immunization, PEG with a weight percentage of 50% and a molecular weight of 1450 is used as a fusogenic agent, and the cell fusion is carried out according to a routine method. Specific steps: under an aseptic condition, the mouse is killed by neck removal, spleen is taken out and crushed with a homogenizer, the spleen cells were separated using a filter screen, mixed with mouse bone marrow cells SP2/0 at a ratio of 5:1, and centrifuged, the mixed cells were re-suspended with a RPMI-1640 basal medium and centrifuged, and a supernatant is abandoned. 1-2 mL of 50% PEG is added totally for 1 min, 10-20 mL of the RPMI-1640 basal medium is added along a wall and centrifuged, the supernatant is abandoned, the fusion cells at the bottom of a tube were re-suspended with 20 mL of cell complete medium containing 1% HAT, the suspended cells were added into a 80 mL semi-solid medium, mixed well, then added onto a 6-well cell culture plate at 1.5 mL/well, and put in a carbon dioxide incubator at 37° C. to incubate. The cell complete medium containing 1% of HAT contains 20% (volume percentage) of fetal calf serum, 75% (volume percentage) of RPMI-1640 basal medium, 1% (weight percentage) of L-glutamine, 1% (volume percentage) of HEPES, 1% (volume percentage) of double antibody (10000 unit/mL penicillin and 10000 μg/mL streptomycin), 2% (volume percentage) of growth factor (HFCS) and 1% (weight percentage) of hypoxanthine-aminopterin-thymidine (i.e., HAT) and methylcellulose (purchased from sigma-Aldrich Company).

Screening and Cloning of Cell Strains 2-3 weeks after the cell fusion, when a cell colon is grown to visible to the naked eyes, the clone is picked up from the medium with a micropipettor, and transferred to a 96-well cell culture plate and incubated using an HAT liquid, and when the cells were grown to ⅔ of the well bottom, an incubated supernatant is absorbed for detection. Using a two-step screening method, a direct ELISA method is adopted in the first step, a positive well which is against diacetoxyscirpenol and not against carrier protein BSA is screened out; the indirect competitive ELISA method is adopted in the second step to detect the positive well screened out in the first step, the diacetoxyscirpenol is used as a competitor, the well in which light absorption value and sensitivity were both high is selected (high light absorption value refers to a well with a competitor of 0, i.e. final measured value of the positive control well is high, high sensitivity refers to when the inhibiting rate is 50% of competitor concentration, i.e. $IC_{50}$ value is small), a sub-cloning is carried out using a limiting dilution method, after the sub-cloning, a detection is carried out using the same two-step method, after the sub-cloning is repeated as such for 4-5 times, a hybridoma cell strain DAS5G11E7 is obtained. The hybridoma cell strain is preserved in China Center for Type Culture Collection (CCTCC) on Apr. 3, 2018, the preservation address is Wuhan University, Wuhan, China, and the accession number is CCTCC NO:C201881.

Antibody variable range sequence determination of an anti-diacetoxyscirpenol monoclonal antibody hybridoma cell strain DAS5G11E7

(1) abstraction of total RNA: a total RNA abstraction kit from Tiangen company is adopted to abstract total RNA capable of producing a hybridoma cell strain DAS5G11E7 according to the instruction book;

(2) synthesis of cDNA: the total RNA obtained in step 1 is used as a template, oligo(dT)15 is used as a primer, reverse transcription is carried out according to Super-Script™-2II reverse transcriptase instruction book, and a cDNA first chain is synthesized, and primer oligo (dT)15 is purchased from Invitrogen;

(3) cloning of variable regions gene by a PCR method: a primer is designed according to conserved site of mouse antibody gene sequence in GENBANK, heavy-chain and light-chain variable region genes of the antibody are amplified using CDNA as the template. PCR procedure is: 94° C. 30 s, 58° C. 45 s, 72° C. 1 min, amplifying is carried out for 30 cycles, and finally extended at 72° C. for 10 min. A PCR product is subjected to electrophoresis separation by 1% (weight percentage) of sepharose, then a DNA fragment is purified and recycled using a kit, and ligated to a carrier pMD18-T, *Escherichia coli* DH5a competent cells were transformed, positive clones were picked up, and sent to Shanghai Sunny Biotech Co. Ltd for sequencing. Sequences of primers are respectively: a primer in a heavy-chain variable region is 5'-CAG GTS MAR CTG MAG GAG TCW G-3'(22mer) and 5'-CAG GGG CCA GTG GAT AGA CAG ATG GGG G-3'(28mer), where S, M, R and W are degenerate bases, M=A/C, R=A/G, S=G/C, W=A/T, and a primer in a light-chain variable region is 5'-GAC ATC AAG ATG ACC CAG TCT CCA-3'(24mer) and 5'-CCG TTT TAT TTC CAG CTT GGT CCC-3'(24mer).

Gene sequence results obtained: a gene sequence length encoded by the heavy-chain variable region is 351 bp, the sequence is as shown in SEQ ID NO:1, it is deduced according to the obtained gene sequence that the heavy-chain variable region encoded by the gene sequence consists of 117 amino acids, and the sequence is as shown in SEQ ID NO:3. A sequence length encoded by the light-chain variable region is 324 bp, the sequence is as shown in SEQ ID NO:2, it is deduced according to the obtained gene sequence that the light-chain variable region encoded by the gene sequence consists of 108 amino acids, and the sequence is as shown in SEQ ID NO:4.

Obtaining of an Anti-Fumonisin B1 Monoclonal Antibody

The anti-fumonisin B1 monoclonal antibody is secreted by a hybridoma cell strain Fm7A11 with an accession number of CCTCC NO.C201636, specifically it is prepared in advance according to the reported method in patent with an application number of 2017101311660, the preparation method includes: the hybridoma cell strain Fm7A11 is injected into a BALB/c mouse pretreated with a Freund's incomplete adjuvant, an ascites of the mouse is collected, the antibody is purified using a caprylic acid-ammonium sulfate method, a specific operation includes: the mouse ascites is filtered with double-layer filter paper, centrifuged at 4° C. under 12000 r/min for more than 15 min, a supernatant is absorbed, the obtained ascites supernatant is mixed with an acetate buffer having 4 times volume of the supernatant, n-caprylic acid is added slowly under stirring, the volume of n-caprylic acid needed per mL ascites is 30-35 μL, and mixing is carried out at room temperature for 30-60 min, standing is carried out at 4° C. for more than 2 h, centrifuging is carried out under 12000 r/min at 4° C. for more than 30 min, a precipitate is abandoned, the obtained supernatant is filtered with double-layer filter paper, then a phosphate buffer having a volume of 1/10 filtrate, a molar concentration of 0.1 mol/L and pH of 7.4 is added, pH of the mixed liquid is adjusted to 7.4 with a 2 mol/L sodium hydroxide solution, ammonium sulfate is slowly added into an ice bath until the final concentration of ammonium sulfate is 0.277 g/mL, standing is carried out at 4° C. for more than 2 h, then centrifuging is carried out under 12000 r/min at 4° C. for more than 30 min, a supernatant is abandoned, the obtained precipitate is re-suspended in a phosphate buffer having a 1/10 volume of the original ascites, a molar concentration of 0.01 mol/L and pH of 7.4, put in a dialysis bag, dialyzed with 0.01 mol/L PBS for two days, and dialyzed with PB for two days, the protein solution in the dialysis bag is taken out, and centrifuged, the supernatant is collected, the precipitate is abandoned, pre-frozen at −70° C., and then put in a lyophilizer for freeze drying. Lyophilized powder i.e., a purified anti-fumonisin $B_1$ monoclonal antibody is collected.

The acetate buffer is obtained by adding water into 0.29 g of sodium acetate and 0.141 mL of acetic acid to a volume of 100 mL; the 0.01 mol/L phosphate buffer is obtained by adding water into 0.8 g of sodium chloride, 0.29 g of disodium hydrogen phosphate dodecahydrate, 0.02 g of potassium chloride and 0.02 g of potassium dihydrogen phosphate to a volume of 100 mL; and the 0.1 mol/L phosphate buffer is obtained by adding water into 8 g of sodium chloride, 2.9 g of disodium hydrogen phosphate dodecahydrate, 0.2 g of potassium chloride and 0.2 g of potassium dihydrogen phosphate to a volume of 100 mL.

Obtaining of an Anti-Zearalenone Monoclonal Antibody

The anti-zearalenone monoclonal antibody is secreted from a hybridoma cell strain 2D3, it is prepared in advance according to the method reported in a patent with an application number of 201310115825.3, the preparation method includes: the hybridoma cell strain 2D3 is injected into BALB/c mouse pretreated with a Freund's incomplete adjuvant, and a mouse ascites is collected, the antibody is purified by a caprylic acid-ammonium sulfate method, the specific operation includes: the mouse ascites is filtered with double-layer filter paper, centrifuged under 12000 r/min at 4° C. for 15 min, a supernatant is absorbed, the obtained ascites supernatant obtained is mixed with 3 times volume of acetate buffer, and n-caprylic acid is added slowly under stirring, the volume of n-caprylic acid needed for per mL ascites is 33 μL, mixing is carried out at room temperature for 30 min, standing is carried out at 4° C. for 2 h, then centrifuging is carried out under 2000 r/min for 30 min, a precipitate is abandoned, the obtained supernatant is filtered with double-layer filter paper, a phosphate buffer having a 1/10 volume of the filtrate, a molar concentration of 0.1 mol/L and pH of 7.4 is added, the pH value of the mixed liquid is adjusted to 7.4 with a 2 mol/L sodium hydroxide solution and pre-cooled at 4° C., ammonium sulfate is added slowly to a final concentration of ammonium sulfate of 0.277 g/mL, standing is carried out at 4° C. for 2 h, then centrifuging is carried out at 4° C. under 12000 r/min for 30 min, the precipitate is abandoned, the obtained precipitate is re-suspended in a 0.01 mol/L phosphate buffer having 1/10 volume of the primary ascites, put in a dialysis bag, and dialyzed in pure water, the fully dialyzed protein solution is put in a freezer at −70° C. for refrigeration, and then subjected to freeze drying in a lyophilizer, lyophilized powder is collected, that is, a purified anti-zearalenone monoclonal antibody is obtained, and the antibody is placed in a freezer at −20° C. for use.

The acetate buffer is obtained by adding water into 0.29 g of sodium acetate and 0.141 mL of acetic acid to a volume of 100 mL; and the 0.1 mol/L phosphate buffer is obtained by adding water into 0.8 g of sodium chloride, 0.29 g of disodium hydrogen phosphate dodecahydrate, 0.02 g of potassium chloride and 0.02 g of potassium dihydrogen phosphate to a volume of 100 mL.

An anti-deoxynivalenol monoclonal antibody is preferably the anti-deoxynivalenol monoclonal antibody having an $IC_{50}$ less than or equal to 15 ppb, such as Shandong Lvdu Biotechnology Co., Ltd, in the embodiment, the anti-deoxynivalenol monoclonal antibody from Shandong Lvdu Biotechnology Co., Ltd is specifically used, and the sensitivity $IC_{50}$ is 12 ppb.

An anti T-2 toxin monoclonal antibody is preferably an anti-T-2toxinmonoclonal antibody having an $IC_{50}$ less than or equal to 2 ng/mL, such as Shandong Lvdu Biotechnology Co., Ltd, in the embodiment, the anti-T-2 toxin monoclonal antibody from Shandong Lvdu Biotechnology Co., Ltd is specifically used, and after detection, the $IC_{50}$ value is 0.8 ng/mL.

Example 2

Preparation of Fumonisin B1, Anguidin, T-2 Toxin, Zearalenone and Vomitoxin Composite Immunoaffinity Column 1. Preparation of a Matrix 1 g of CNBr activated sepharose lyophilized matrix powder (per gram lyophilized matrix powder may form 3.5 mL final volume of a swollen matrix) is weighed, and dissolved in 1 mmol/L HCl. The matrix would be swollen immediately, then placed in a sintered glass filter and washed with 1 mmol/L HCl for 15 min.

2. Ligand (antibody) coupling a. The above fumonisin B1 antibody, anguidin, T-2 toxin antibody, zearalenone antibody and vomitoxin antibody to be coupled were dissolved in a buffer 0.2 mol/L $NaHCO_3$ with pH of 8.3, the concentration of each antibody is 12.5 mg/mL, and the dissolved antibody is put in an ice bath for temporary storage. The above coupling buffer containing the antibodies is added into a fully sealable container with a lid. The CNBr activated sepharose is quickly transferred to the antibody solution. Under room temperature condition (20-25° C.), the above mixture is mixed fully for 2-4 h.

b. Calculation of a coupling rate: centrifuging is carried out under 2,000 rpm, the sepharose is centrifuged to bottom of a tube, the supernatant is transferred to new centrifugal tube, and a protein content value in the supernatant is measured. The coupling rate is calculated as 98.5% (indicating the coupling is very successful). The sepharose centrifuged to the bottom of the tube is taken, washed with the coupling buffer, and excess ligands were removed.

c. Blocking: the matrix is transferred to a 0.1 mol/L Tris-HC buffer. Under a room temperature condition, standing is carried out for 2-4 h, and all the remaining active groups were blocked.

d. In order to remove excess ligands that were not coupled after the coupling, the matrix is washed successively with a buffer having pH of 4 and a buffer having pH of 8, i.e., 0.1 mol/L acetic acid/sodium acetate buffer and 0.1 mol/L Tris-HCl buffer, and washed at least for three cycles, and the usage amount of each buffer is at least 5 times the matrix volume. In each wash cycle step: firstly washed with 0.1 mol/L acetic acid/sodium acetate buffer, followed by washed with 0.1 mol/L Tris-HCl buffer. Washing is carried out with 0.01% $NaN_3$—PBS of 5 times the gel volume, and preserving is carried out with 0.01% $NaN_3$—PBS.

3. In the packing, seriflux is prepared using a binding buffer, and mixed at a ratio of 75% of a settled matrix and 25% of a phosphate buffer (pH of 7.0). The seriflux is poured into the column by a continuous operation. A column filling operation is carried out using a glass rod leaning on the inner wall of the column, which will help to reduce bubble formation. After the column filling, an opening at a lower end of the affinity column is closed, and a top part of the affinity column is taken down. Operated carefully, a PBS buffer of pH of 7.0 is added to the remainder of the affinity column, so as to form one upward meniscus at a top end of the affinity column. A sieve plate at the top end is inserted into the affinity column at a certain angel, and it is ensured that there is no air beneath the sieve plate. The sieve plate is locked at an appropriate location on the matrix surface, an opening under the affinity column is opened, aseptically-filtrated 0.01% $NaN_3$-PBS of 5 times the column bed volume is passed through the column, and preserved using 0.01% $NaN_3$-PBS, so far the fumonisin B1, anguidin, T-2 toxin, zearalenone and vomitoxin affinity column is filled and equilibrated and can be directly used.

Example 3: Detection of Fumonisin B1, Anguidin, T-2 Toxin, Zearalenone and Vomitoxin in Rice 1.0 Detection of Fumonisin B1, Anguidin, T-2 Toxin, Zearalenone and Vomitoxin in Rice In a rice addition and recovery experiment, three concentration gradients of 500 μg/kg, 1000 μg/kg and 2000 μg/kg of fumonisin B1 and three concentration gradients of 10 μg/kg, 20 μg/kg and 50 μg/kg anguidin, T-2 toxin, zearalenone and vomitoxin were respectively added. In each experiment, five groups of parallel tests were done.

Three Gradients:

Addition amount in the first experiment: 500 μg/kg of fumonisin B1, 10 μg/kg of anguidin, 10 μg/kg of T-2 toxin, 10 μg/kg of zearalenone and 10 μg/kg of vomitoxin.

Addition amount in the second experiment: 1000 μg/kg of fumonisin B1, 20 μg/kg of anguidin, 20 μg/kg of T-2 toxin, 20 μg/kg of zearalenone and 20 μg/kg of vomitoxin.

Addition amount in the third experiment: 2000 μg/kg of fumonisin B1, 50 μg/kg of anguidin, 50 μg/kg of T-2 toxin, 50 μg/kg of zearalenone and 50 μg/kg of vomitoxin.

Abstraction of fumonisin B1, anguidin, T-2 toxin, zearalenone and vomitoxin in rice:

20.0 g of finely ground (particle size less than 2 mm) sample is precisely weighed and put into a homogenizer, 100 mL of acetonitrile/water/formic acid (80+18+2) is added, agitated homogeneously at a high speed and abstracted for 2 min. Filtering is carried out with quantitative filter paper, 5.0 mL of filtrate is precisely transferred, 15.0 mL of PBS solution of pH of 7.0 is added to dilute, filtered with glass fiber filter paper for 1-2 times, until the filtrate is clear. The composite immunoaffinity column is connected to a 10.0 mL glass syringe. 10.0 mL of sample abstracted liquid is precisely transferred and injected into a glass syringe, an air pressure pump is connected with the glass syringe, the pressure is regulated such that the solution slowly passes through the composite immunoaffinity column at a flow rate of about 6 mL/min, until 2-3 mL of air passes through the column body. The column is rinsed with 10.0 mL of water twice, all the effluent is abandoned, and 2 mL-3 mL of air passes through the column body. 1.0 mL of chromatographic grade methanol is added precisely for elution, the flow rate is 1 mL/min-2 mL/min, and all the eluent is collected in a glass test tube for detection.

2.0 Conditions for High-Performance Liquid Chromatography-Mass Spectrometry a. mobile phase: A, a 0.05% formic acid/water solution; B, a 0.05% formic acid/acetonitrile solution
b. gradient elution: 0-3 min, 15%-50% of B; 4-5 min, 50%-70% of B; 6.5-8 min, 70%-100% of B; 8-10 min, 100%-50% of B; 10-11 min, 50%-15% of B; and 11-15 min, 15% of B.
c. chromatographic column: a C-18 column (column length of 50 mm, inner diameter of 2.1 mm, and filler diameter of 1.7 μm)
d. flow rate: 200 μL/min
e. mass spectrometry scanning parameters of various toxin detection are as shown in Table 1.

3.0. Quantitative Determination

Standard working solutions of fumonisin B1, anguidin, T-2 toxin, zearalenone and vomitoxin with different concentrations were absorbed using a sample injector, the fumonisin B1 (5000, 2500, 1000, 200, 50, 5 and 1 μg/kg), anguidin (100, 50, 25, 10, 5, 1 and 0.1 μg/kg), T-2 toxin (100, 50, 25, 10, 5, 1 and 0.1 μg/kg); zearalenone (100, 50, 25, 10, 5, 1 and 0.1 μg/kg), and vomitoxin (100, 50, 25, 10, 5, 1 and 0.1 μg/kg) were injected into a high-performance liquid chromatograph-mass spectrometer, peak area of the standard solutions were measured under the above conditions, standard curves of various toxins were drawn, and then content of each toxin were calculated by an external standard method.

4.0. Results

Recovery rate results of addition in rice were all between 82.5-109.1%, RSD were all less than 10%. The results indicate that the method fully meets the analysis requirements of fumonisin B1, anguidin, T-2 toxin, zearalenone and vomitoxin detection in rice. The results are respectively seen in Table 3-Table 7.

TABLE 3

Results of recovery rate of adding fumonisin $B_1$ in rice

| Adding concentration of fumonisin $B_1$ μg/kg | Re-covery rate 1 % | Re-covery rate 2 % | re-covery rate 3 % | re-covery rate4 % | Re-covery rate 5 % | RSD % |
|---|---|---|---|---|---|---|
| 500 | 103.1 | 100.3 | 87.5 | 91.3 | 94.6 | 6.5 |
| 1000 | 93.6 | 100.1 | 87.2 | 83.2 | 93.1 | 7.3 |
| 2000 | 88.2 | 95.7 | 98.1 | 84.2 | 86.1 | 5.4 |

TABLE 4

Results of recovery rate of adding anguidin in rice

| Adding concen-tration of anguidin μg/kg | Re-covery rate 1 % | Re-covery rate 2 % | Re-covery rate 3 % | Re-covery rate 4 % | Re-covery rate 5 % | RSD % |
|---|---|---|---|---|---|---|
| 10 | 99.6 | 103.3 | 104.1 | 100.5 | 104.6 | 4.9 |
| 20 | 94.2 | 102.9 | 105.6 | 104.9 | 92.3 | 3.9 |
| 50 | 85.1 | 95.3 | 112.1 | 105.3 | 96.1 | 7.3 |

TABLE 5

Results of recovery rate of adding T-2 toxin in rice

| Adding concen-tration of T-2 toxin μg/kg | Re-covery rate 1 % | Re-covery rate 2 % | Re-covery rate 3 % | Re-covery rate 4 % | Re-covery rate 5 % | RSD % |
|---|---|---|---|---|---|---|
| 10 | 107.9 | 99.8 | 96.5 | 96.5 | 98.3 | 7.4 |
| 20 | 99.3 | 93.2 | 89.3 | 86.3 | 99.1 | 8.6 |
| 50 | 89.7 | 87.4 | 97.2 | 97.2 | 97.2 | 7.9 |

TABLE 6

| Results of recovery rate of adding zearalenone in rice | | | | | | |
|---|---|---|---|---|---|---|
| Adding concentration of zearalenone μg/kg | Recovery rate 1 % | Recovery rate 2 % | Recovery rate 3 % | Recovery rate 4 % | Recovery rate 5 % | RSD % |
| 10 | 109.1 | 98.3 | 100.1 | 99.3 | 81.6 | 8.9 |
| 20 | 99.4 | 91.1 | 98.3 | 91.4 | 82.5 | 7.1 |
| 50 | 98.7 | 90.8 | 104.4 | 101.2 | 98.6 | 6.7 |

TABLE 7

| Results of recovery rate of adding vomitoxin in rice | | | | | | |
|---|---|---|---|---|---|---|
| Adding concentration of vomitoxin μg/kg | Recovery rate 1 % | Recovery rate 2 % | Recovery rate 3 % | Recovery rate 4 % | Recovery rate 5 % | RSD % |
| 10 | 85.3 | 102 | 99.7 | 91.4 | 97.9 | 6.9 |
| 20 | 98.5 | 92.9 | 92.2 | 89.6 | 94.4 | 7.0 |
| 50 | 89.5 | 96.3 | 95.6 | 96.8 | 86.5 | 4.9 |

Example 4: Detection of Fumonisin B1, Anguidin, T-2 Toxin, Zearalenone and Vomitoxin in Edible Oil 1.0. Detection of Fumonisin B1, Anguidin, T-2 Toxin, Zearalenone and Vomitoxin in Edible Oil In an edible oil addition and recovery experiment, three concentration gradients of 500 μg/kg, 1000 μg/kg and 2000 μg/kg fumonisin B1 and 10 μg/kg, 20 μg/kg and 50 μg/kg of anguidin, T-2 toxin, zearalenone and vomitoxin were added respectively. In each experiment, five groups of parallel tests were done.

Abstraction of fumonisin B1, anguidin, T-2 toxin, zearalenone and vomitoxin in edible oil:

Abstraction of vegetable oil liquid sample: 5.0 g of a vegetable oil sample is precisely weighed into a 50 mL centrifugal tube, 15.0 mL of 70% methanol water solution is added, shaken and mixed well for 2 min in a Vortex mixer, centrifuged under 5000 r/min for 2 min, 10.0 mL of an ethanol solution layer is transferred, diluted with 20.0 mL of water, mixed well in a mixer, and filtered through glass fiber filter paper, until the filtrate is clear. The composite immunoaffinity column is connected to a 10.0 mL glass syringe. 10.0 mL of sample abstraction liquid is precisely transferred and injected into the glass syringe, an air pressure pump is connected with the glass syringe, the pressure is adjusted such that the solution slowly passes though the composite immunoaffinity column at a flow rate of about 6 mL/min, until 2-3 mL of air passes through the column body. The column is rinsed with 10.0 mL of water twice, all the effluent is abandoned, and 2 mL-3 mL air passes through the column body. 1.0 mL of chromatographic grade methanol is added precisely for eluting, the flow rate is 1 mL/min-2 mL/min, and all the eluent is collected in a glass test tube for detection.

2.0. Conditions for High-Performance Liquid Chromatography-Mass Spectrometry a. mobile phase: A, a 0.05% formic acid/water solution; B, a 0.05% formic acid/acetonitrile solution b. gradient elution: 0-3 min, 15%-50% of B; 4-5 min, 50%-70% of B; 6.5-8 min, 70%-100% of B; 8-10 min, 100%-50% of B; 10-11 min, 50%-15% of B; and 11-15 min, 15% of B.

c. chromatographic column: a C-18 column (column length of 50 mm, inner diameter of 2.1 m, and filler diameter of 1.7 μm)

d. flow rate: 200 μL/min e. mass spectrometry scanning parameters of various toxin detection are as shown in Table 1.

3.0. Quantitative Determination

Standard working solutions of fumonisin B1, anguidin, T-2 toxin, zearalenone and vomitoxin with different concentrations were absorbed by a sample injector and injected into a high-performance liquid chromatograph-mass spectrometer, peak area of the standard solutions were measured under the above conditions, standard curves of various toxins were drawn, and then content of each toxins were calculated using an external standard method.

4.0. Results.

Recovery rate results of addition in vegetable oil are all between 88.5-109.2%, RSD are all smaller than 10%. The results indicate that the method fully meets the analysis requirements for fumonisin B1, anguidin, T-2 toxin, zearalenone and vomitoxin detection in rice.

The results are respectively seen in Table 8-Table 12.

TABLE 8

| Results of the recovery rate of adding fumonisin B1 in vegetable oil | | | | | | |
|---|---|---|---|---|---|---|
| Adding concentration of fumonisin B1 μg/kg | Recovery rate 1 % | Recovery rate 2 % | Recovery rate 3 % | recovery rate4 % | recovery rate5 % | RSD % |
| 500 | 104.7 | 103.9 | 105.5 | 103.1 | 101.7 | 4.1 |
| 1000 | 99.4 | 86.9 | 96.7 | 104.5 | 105.2 | 5.4 |
| 2000 | 88.5 | 89.1 | 93.2 | 102.7 | 97.9 | 68 |

TABLE 9

| Results of recovery rate of adding anguidin in vegetable oil | | | | | | |
|---|---|---|---|---|---|---|
| Adding concentration of anguidin μg/kg | Recovery rate 1 % | Recovery rate 2 % | Recovery rate 3 % | Recovery rate 4 % | Recovery rate 5 % | RSD % |
| 10 | 95.5 | 109.2 | 99.6 | 105.6 | 107.3 | 6.1 |
| 20 | 97.3 | 99.2 | 102.4 | 93.2 | 96.3 | 6.3 |
| 50 | 96.3 | 98.2 | 98.2 | 97.4 | 92.2 | 5.5 |

TABLE 10

| Results of recovery rate of adding T-2 toxin in vegetable oil | | | | | | |
|---|---|---|---|---|---|---|
| Adding concentration of T-2 toxin μg/kg | Recovery rate 1 % | Recovery rate 2 % | Recovery rate 3 % | Recovery rate 4 % | Recovery rate 5 % | RSD % |
| 10 | 106.2 | 101.1 | 97.3 | 101.4 | 103.2 | 5.4 |
| 20 | 100.5 | 98.5 | 91.3 | 99.5 | 98.1 | 5.5 |
| 50 | 97.6 | 90.4 | 101.1 | 102.3 | 92.3 | 6.3 |

TABLE 11

| Adding concentration of Zearalenone μg/kg | Re-covery rate 1 % | Re-covery rate 2 % | Re-covery rate 3 % | Re-covery rate 4 % | Re-covery rate 5 % | RSD % |
|---|---|---|---|---|---|---|
| Results of recovery rate of adding zearalenone in vegetable oil | | | | | | |
| 10 | 91.5 | 106.2 | 89.3 | 90.8 | 95.0 | 6.1 |
| 20 | 92.4 | 96.1 | 107.0 | 96.2 | 101.6 | 5.8 |
| 50 | 89.3 | 98.2 | 97.4 | 98.5 | 96.1 | 5.5 |

TABLE 12

| Adding concentration of Vomitoxin μg/kg | Re-covery rate 1 % | Re-covery rate 2 % | Re-covery rate 3 % | Re-covery rate 4 % | Re-covery rate5 % | RSD % |
|---|---|---|---|---|---|---|
| Results of recovery rate of adding vomitoxin in vegetable oil | | | | | | |
| 10 | 94.2 | 106.4 | 97.3 | 98.3 | 99.5 | 6.8 |
| 20 | 92.2 | 97.3 | 89.2 | 96.7 | 101.2 | 6.4 |
| 50 | 89.3 | 97.8 | 89.6 | 92.1 | 97.1 | 5.2 |

What is claimed is:

1. An immunoadsorbent for purifying fumonisin B1, anguidin, T-2 toxin, zearalenone, and vomitoxin, the immunoadsorbent comprises a solid phase carrier, and an anti-fumonisin B1 monoclonal antibody, an anti-anguidin monoclonal antibody, an anti-T-2 toxin monoclonal antibody, an anti-zearalenone monoclonal antibody, and an anti-vomitoxin monoclonal antibody which are coupled to the solid phase carrier, and the anti-anguidin monoclonal antibody is a monoclonal antibody secreted by a hybridoma cell strain DAS5G11E7 having an accession number of CCTCCNO: C201881.

2. The immunoadsorbent according to claim 1, wherein the solid phase carrier is sepharose.

3. The immunoadsorbent according to claim 1, wherein $IC_{50}$ of the anti-vomitoxin monoclonal antibody is less than or equal to 15 ppb; $IC_{50}$ of the anti-T-2 toxin monoclonal antibody is less than or equal to 2 ppb; the anti-fumonisin B1 monoclonal antibody is selected from a monoclonal antibody secreted by a hybridoma cell strain Fm7A11 having an accession number of CCTCC NO.C201636; and the anti-zearalenone monoclonal antibody is selected from a monoclonal antibody secreted by a hybridoma cell strain 2D3 having an accession number of CCTCC NO.C201328.

4. A composite affinity column for purifying fumonisin B1, anguidin, T-2 toxin, zearalenone, and vomitoxin, the composite affinity column being loaded with the immunoadsorbent for purifying fumonisin B1, anguidin, T-2 toxin, zearalenone, and vomitoxin according to claim 1.

5. A preparation method of the composite affinity column according to claim 4, comprising the following steps:

a) matrix treatment washing CNBr-activated sepharose matrix powder with HCl at a pH of 2-3 to remove impurities;

b) ligand coupling dissolving a fumonisin B1 monoclonal antibody, an anguidin monoclonal antibody, a T-2 toxin monoclonal antibody, a zearalenone monoclonal antibody, and a vomitoxin monoclonal antibody to be coupled by using a coupling buffer to obtain antibody solutions, quickly transferring the sepharose matrix activated in the step a) to the above antibody solutions, and carrying out coupling;

c) ligand blocking blocking all remaining active groups;

d) removing excess ligands that are not coupled after the coupling; and e) packing.

6. The preparation method of the composite affinity column according to claim 5, wherein the washing is carried out with HCl having a concentration of 1 mmol/L for 15 min in the step a); and the coupling buffer in the step b) is 0.2 mol/L $Na_2HCO_3$ with a pH of 8.3.

7. The preparation method of the composite affinity column according to claim 5, wherein the concentration of each antibody solution in the step b) is 10-15 mg/mL; and a coupling condition in the step b) comprises: fully mixing the above mixture under a room temperature condition of 20-25° C. for 2-4 h.

8. The preparation method of the composite affinity column according to claim 5, wherein a process of the ligand blocking in the step c) comprises: transferring the sepharose matrix treated by the step b) to a 0.1 mol/L Tris-HCl buffer, and standing for 2-4 h under a room temperature condition.

9. The preparation method of the composite affinity column according to claim 5, wherein the step d) comprises: successively washing the sepharose matrix treated by the step c) with a buffer solution with a pH value of 4 and a buffer solution with a pH value of 8 for at least three cycles;

wherein the buffer solution with a pH value of 4 and the buffer solution with a pH value of 8 may be respectively selected from 0.1 mol/L acetic acid/sodium acetate buffer and 0.1 mol/L Tris-HCl buffer; and after treatment in the step d), washing is carried out with 0.01% $NaN_3$-PBS of which the amount is 5 times the volume of the sepharose, preserving is carried out by using 0.01% $NaN_3$—PBS, and then packing is carried out.

10. A method for detecting the content of fumonisin B1, anguidin, T-2 toxin, zearalenone, and vomitoxin based on the composite affinity column of claim 4, comprising adsorbing fumonisin B1, anguidin, T-2 toxin, zearalenone, and vomitoxin by an immunoadsorbent, other impurities flowing out of the composite affinity column when a sample to be detected is allowed to pass through the composite affinity column of claim 4, then eluting the composite affinity column with chromatographic grade methanol, and collecting an eluate for detection in a high performance liquid chromatograph-mass spectrometer to obtain the content of each toxin.

* * * * *

SEQUENCE LISTING

```
<160> NUMBER OF SEQ ID NOS: 4

<210> SEQ ID NO 1
<211> LENGTH: 351
<212> TYPE: DNA
<213> ORGANISM: Mice

<400> SEQUENCE: 1

gaagtgcaac tggtggagtc tgggggagac ttagtgaagc ctggagggtc cctgaaactc      60

tcctgttcag cctccggatt cactttcaat tactatggca tgtcttgggt tcgccagact     120

ccagacaacc tcctggagtg ggtcgcaggc attagtagtg gtggttctta cacctattat     180

tctgacagtg tgaagggacg attcaccatc tccagagaca gtgccacgaa caccctgtac     240

ctgcaaatga ccagtctgaa gtctcaagac acagccatgt attattgtat tagactcccg     300

tttgggtcta tggactattg gggtcaagga accgcagtca ccgtctcctc a              351


<210> SEQ ID NO 2
<211> LENGTH: 324
<212> TYPE: DNA
<213> ORGANISM: Mice

<400> SEQUENCE: 2

caggctgttg tgactcagga acctgcactc accacatcac ctggtgaaac agtcacactc      60

acttgtcgct caagtactgg ggctgtaaca actggtaatt atgtcaactg ggtccaagag     120

aaaccagatc atttattcag tggtctaata ggtaatacca ataaccgagc tccaggtgtt     180

cctgccagat tctcaggctc cctgattgga gacaaggctg ccctcaccat cacagggaca     240

cagactgagg atgaggcaat atatttctgt gctctatggt acaccgacca tttggtgttc     300

ggtggaggaa ccaaattgac tgtc                                            324


<210> SEQ ID NO 3
<211> LENGTH: 117
<212> TYPE: PRT
<213> ORGANISM: Mice

<400> SEQUENCE: 3

Glu Val Gln Leu Val Glu Ser Gly Gly Asp Leu Val Lys Pro Gly Gly
1               5                   10                  15

Ser Leu Lys Leu Ser Cys Ser Ala Ser Gly Phe Thr Phe Asn Tyr Tyr
            20                  25                  30

Gly Met Ser Trp Val Arg Gln Thr Pro Asp Asn Leu Leu Glu Trp Val
        35                  40                  45

Ala Gly Ile Ser Ser Gly Gly Ser Tyr Thr Tyr Tyr Ser Asp Ser Val
    50                  55                  60
```

-continued

```
Lys Gly Arg Phe Thr Ile Ser Arg Asp Ser Ala Thr Asn Thr Leu Tyr
65                  70                  75                  80

Leu Gln Met Thr Ser Leu Lys Ser Gln Asp Thr Ala Met Tyr Tyr Cys
                85                  90                  95

Ile Arg Leu Pro Phe Gly Ser Met Asp Tyr Trp Gly Gln Gly Thr Ala
            100                 105                 110

Val Thr Val Ser Ser
        115


<210> SEQ ID NO 4
<211> LENGTH: 108
<212> TYPE: PRT
<213> ORGANISM: Mice

<400> SEQUENCE: 4

Gln Ala Val Val Thr Gln Glu Pro Ala Thr Thr Thr Ser Pro Gly Glu
1               5                   10                  15

Thr Val Thr Leu Thr Cys Arg Ser Ser Thr Gly Ala Val Thr Thr Gly
            20                  25                  30

Asn Tyr Val Asn Trp Val Gln Glu Lys Pro Asp His Leu Phe Ser Gly
        35                  40                  45

Leu Ile Gly Asn Thr Asn Asn Arg Ala Pro Gly Val Pro Ala Arg Phe
    50                  55                  60

Ser Gly Ser Leu Ile Gly Asp Lys Ala Ala Leu Thr Ile Thr Gly Thr
65                  70                  75                  80

Gln Thr Glu Asp Glu Ala Ile Tyr Phe Cys Ala Leu Trp Tyr Thr Asp
                85                  90                  95

His Leu Val Phe Gly Gly Gly Thr Lys Leu Thr Val
            100                 105
```